United States Patent [19]
Fields et al.

[11] Patent Number: 5,340,403
[45] Date of Patent: Aug. 23, 1994

[54] PROCESS FOR THE PRODUCTION OF XYLOSE

[75] Inventors: Peter R. Fields; Robin J. Wilson, both of Stockton-on-Tees, United Kingdom

[73] Assignee: Zeneca Limited, London, United Kingdom

[21] Appl. No.: 670,386

[22] Filed: Mar. 15, 1991

Related U.S. Application Data

[63] Continuation of Ser. No. 432,352, Nov. 6, 1989, abandoned, which is a continuation of Ser. No. 110,661, Oct. 20, 1987, abandoned.

[30] Foreign Application Priority Data

Oct. 20, 1986 [GB] United Kingdom ............... 8625095

[51] Int. Cl.$^5$ .................... C13K 1/02; C13K 1/04
[52] U.S. Cl. ................................. 127/37; 127/58; 127/60; 127/61
[58] Field of Search ............... 127/37, 1, 58, 60, 61

[56] References Cited

U.S. PATENT DOCUMENTS

| | | | |
|---|---|---|---|
| 2,759,856 | 8/1956 | Saums et al. | 127/37 |
| 2,959,500 | 11/1960 | Schlapfer et al. | 127/37 |
| 3,219,484 | 11/1965 | Smythe et al. | 127/60 |
| 3,565,687 | 2/1971 | Suminoe et al. | 127/37 |
| 3,579,380 | 5/1972 | Friese | 127/37 |
| 3,784,408 | 1/1974 | Jaffe et al. | 127/37 |
| 3,990,904 | 11/1976 | Friese et al. | 127/37 |
| 4,008,285 | 2/1977 | Melaja et al. | 127/37 |
| 4,102,705 | 7/1978 | Pfeiffer et al. | 127/37 |

OTHER PUBLICATIONS

McCase et al, *Unit Operation of Chemical Engineering*, McGraw-Hill, N.Y., 1985, pp. 799-806.

*Primary Examiner*—David Brunsman
*Attorney, Agent, or Firm*—Cushman, Darby & Cushman

[57] ABSTRACT

A process for producing xylose from a ligno-cellulosic material comprising xylan-containing hemicellulose in which the ligno-cellulosic material is subjected initially to the three steps (1) hydrolysis to produce an aqueous xylose-containing medium and an insoluble residue; (2) separation of the insoluble residue from the medium; and (3) treatment of the medium to remove organic and/or inorganic nutrients therefrom. The medium is thereafter concentrated to a syrup having a water content in the range 20% to 40% by weight which is then mixed with ethanol and the xylose is separated from the ethanolic solution.

12 Claims, 3 Drawing Sheets

PROCESS FOR THE PRODUCTION OF XYLOSE

This is a continuation of Application No. 07/432,352, filed on Nov. 6, 1989, which was abandoned upon the filing hereof which is a continuation of 07/110,661, filed Oct. 20, 1987, now abandoned.

This invention relates to a process for the production of xylose.

Xylose is a pentose sugar which is used in the production of xylitol and other sweetening additives for foods. It is prepared by the acid hydrolysis of ligno-cellulosic materials containing hemicelluloses having a high proportion of xylose units or xylans in their molecules. In addition to hemicelluloses, ligno-cellulosic material to contain lignin, cellulose and other carbohydrates. Furthermore hemicellulose molecules contain, in addition to xylans, units of other sugars. Hemicelluloses derived from different ligno-cellulosic materials vary in structure, some containing a greater proportion of xylans in their molecules than are contained in the molecules of other hemicelluloses. In the production of xylose it is necessary to separate lignin, cellulose and other materials from the product of the initial hydrolysis. Known processes for the production of xylose from ligno-cellulosic materials include that proposed in U.S. Pat. No. 3,784,408 which includes a separation having a final step in which xylose is recovered as a crystalline precipitate from a methanolic solution.

In the production of xylose from ligno-cellulosic materials on a commercial scale it is important that as little as possible of the xylose available in the starting materials is lost during separation from the other products of hydrolysis. Generally in processes previously used to produce xylose, separation has only been achieved with great difficulty and high losses. This has considerably limited the commercial value of the processes generally used to date.

According to the present invention we provide a process for the production of xylose from a ligno-cellulosic material comprising a xylan-containing hemicellulose, which comprises the steps of:
(1) hydrolysing the ligno-cellulosic material with an aqueous acid to produce an aqueous xylose-containing medium and an insoluble residue comprising lignin and cellulose;
(2) separating the insoluble residue from the xylose-containing medium;
(3) treating the xylose-containing medium to remove organic and/or ionic contaminents therefrom;
(4) concentrating the xylose-containing medium to a syrup having a water content in the range 20% to 40% by weight; and
(5) mixing the syrup with ethanol to form an ethanolic solution and crystallizing xylose from the ethanolic solution.

Preferably the crystals produced in step (5) are washed with aqueous ethanol in order to improve purity and to meet further processing criteria. Most suitably the aqueous ethanol is an ethanol/water mixture containing 90% ethanol.

After either step (2) or step (3) a post hydrolysis step may be performed to remove or reduce any oligosaccharides present. The reaction described in step (1) can be carried out in batch or continuous mode. If it is carried in continuous mode then the residue time distribution of the continuous reactor could give rise to incomplete hydrolysis of the hemicellulose to sugar monomers. The present of hemicellulosic oligosaccharides can lead to problems during the subsequent crystalisation of xylose. Thus, to reduce this problem, a post-hydrolysis step may be employed to remove or reduce the oligosaccharide content. This would take the form of heating the xylose containing liquor to a temperature of between 50°–150° C. for a period within the range of 2 mins to 2 hours in the presence of a dilute acid of 0.5 to 5% in concentration. This would take place in a reactor with a discrete residence time such as a plug flow or batch reactor. In a commercial process a routine analysis can determine the amount of oligosaccharides present in order that it can be decided if post hydrolysis is required.

Suitably the ligno-cellulosic material is one containing hemicelluloses having a high proportion of xylans in their molecules. Examples of suitable materials include wheat straw, corn stover and bagasse.

The hydrolysis step (1) is suitably carried out using a dilute aqueous solution of an acid. Preferably a solution containing 0.5% to 5% acid in water is used. The acid may be an inorganic acid such as sulphuric acid, hydrochloric acid or phosphoric acid or an organic acid such as acetic acid or trifluoracetic acid. During hydrolysis the reaction mixture is suitably maintained at a temperature within the range 70° to 270° C., temperatures within the range 100° to 150° C. being preferred. Hydrolysis is preferably carried out for a period within the range 2 minutes to 2 hours. For the hydrolysis step a suitable combination of process parameters is selected. For instance when higher temperatures are used, hydrolysis is preferably carried out using weaker solutions of acids and/or for shorter periods of time. Combinations of parameters at the upper ends of the suitable ranges, i.e. high temperatures for longer periods using stronger solutions of acids, are not preferred since under such combinations of conditions there exists the possibility of breakdown of the cellulose and/or lignin content of the ligno-cellulosic material which is not desirable. Such combinations of severe conditions may also cause degradation of the xylose produced to some extent. The hydrolysis step causes breakdown of hemicellulose molecules to produce xylans which are hydrolysed to add molecules of water and thereby produce xylose molecules. Any proteins or lipids which are released as a result of the hydrolysis go into solution. Lignin and cellulose are not affected and do not go into solution. These insoluble materials are separated in separation step (2). Any suitable separation method may be used in step (2), filtration being very suitable.

After separation of the insoluble residue containing cellulose and lignin, the aqueous xylose-containing medium is treated in removal step (3) to remove organic and/or ionic contaminents therefrom. The xylose-containing medium may be treated to remove organic or ionic contaminents in either order but preferably organic contaminents are removed first. The most significant organic contaminents are proteinaceous materials, lipids and coloured materials. The organic contaminents may be removed by any suitable method, e.g. treatment with reagents such as activated charcoal or polymeric absorbents. The treatment reagent may be contained in a bed through which the aqueous medium is passed or the reagent may be added to the medium in a tank. The most significant ionic contaminent is the acid used in hydrolysis step (1) but other inorganic contaminents may also be present. Removal of inorganic contaminents can be achieved by treatment with an electro-dialyser and/or a suitable ion-exchange resin, any conventional cationic or anionic ion-exchange resins being suitable. A combination of the electro-dialyser and the ion-exchange resin treatments can be used, the xylose-containing medium being subjected first to electro-dialyser treatment followed by passage through a bed of ion-exchange resin.

Suitable anionic ion-exchange resins for use in removal step (3) include resins formed from cross-linked polystyrene containing quaternary ammonium groups or substituted amines, polycondensation products of phenol and formaldehyde, polymerisation products of aromatic amines and formaldehyde guanidine-formaldehyde resins and polyamines. These anionic ion-exchange resins are commercially available as, for example, "AMBERLITE" (Registered Trade Mark) types IR-4B and IRA-400, "DOWEX" (Registered Trade Mark) types 1 and 2 and "PERMUTIT" (Registered Trade Mark) types S and D.R.

Suitable cationic ion exchange resins include polystyrene sulphonic acid type resins such as "AMBERLITE" IR-120 and "DOWEX" 50.

The xylose-containing medium passing to concentration step (4) is typically a solution containing 1% to 50% by weight xylose. In step (4) this solution is concentrated to a thick syrup having a water content in the range 20% to 40% by weight with the preferred range being 30% to 37% by weight. It is possible to operate the process using water contents below 30% by weight based on a decision to compromise between purity and yield, Below 20% by weight the syrup becomes too viscous for practical operation. Such a syrup is sufficiently concentrated to enable xylose to crystallise out when the syrup is mixed with ethanol in crystallization step (5). Concentration of the xylose-containing medium is carried out under conditions such that any significant degradation of zylose is avoided. Evaporation, particularly rotary or falling film evaporation, is preferred.

The syrup produced by concentration step (4) typically has a temperature in the range 10° C. to 65° C., preferably in the range 10° C. to 20° C., when it passes to crystallization step (5). In the crystallisation step, which is preferably carried out at ambient temperature, ethanol is added to the syrup, Suitably not more than 2 volumes of ethanol are added per volume of syrup. The addition of 0.5 to 2 volumes of ethanol per volume of syrup preferred with addition of I volume ethanol to 1 volume of syrup being especially suitable. The ethanol/syrup mixture is allowed to stand for a period, suitably 10 to 18 hours, with occasional shaking to allow xylose to crystallize. It is possible to improve the crystallization process by seeding with xylose crystals, It is found that the ethanol will preferentially dissolve the hydrolysed materials which have passed through the various purification stages without dissolving a substantial amount of xylose which is sparingly soluble in ethanol is less soluble in this solvent than are other sugars. Thus the xylose which crystallizes has a high degree of purity. After crystallization of xylose the remaining aqueous liquor may be re-cycled, e.g. to step (3) and subjected to further extraction. In step (5) it is preferred to add ethanol to the syrup to avoid too great an amount of ethanol being present temporarily.

The process of the invention is advantageous In that xylose losses during the separation are reduced and a high proportion of the xylose present as xylan in the ligno-cellulosic material is extracted.

The invention is illustrated by the following Examples:

EXAMPLE 1

1 kg of wheat straw was treated with 9 l of a weak (2%) aqueous solution of sulphuric acid for 30 mins. at a temperature of 130° C. From the resultant mixture the insoluble residue comprising lignin and cellulose was separated by filtration. After separation of the insoluble residue, the aqueous medium was treated with activated charcoal (2.5 g charcoal per 100 mls medium) to remove organic contaminents. The medium was then filtered through a glass filter paper leaving contaminated activated charcoal behind. Thereafter the medium was neutralised with sodium hydroxide and electrodialized. After this treatment the medium at a temperature of 50° C. was subjected to rotary evaporation to produce 256 g of a thick viscous syrup. Using a Silverson mixer this syrup was mixed with 200 ml ethanol and the resulting mixture was allowed to stand at room temperature (20° C.) for 24 hours with occasional shaking. Seeding was found to be unnecessary in this instance. After 24 hours crystallization of xylose had taken place and 138 g of crystals were filtered off and washed with cooled ethanol before being air-dried. After analysis by high performance liquid chromatography the material was found to contain 93.4% xylose by weight, corresponding to a yield of 12.8% of xylose upon the weight of the straw.

EXAMPLE 2

A batch of hemicellulosic sugar syrup was extracted from chopped wheat straw in a 250 liter batch reactor. The hydrolysis reaction occurred in a weak aqueous solution of sulphuric acid held at 130° C. for 30 mins. The resultant mixture was filtered and the filtrate treated with activated carbon followed by neutralisation with sodium hydroxide. The syrup was then electrodialysed to remove the bulk of any ionic contaminants. The liquor was then concentrated in a falling film evaporator to provide a supply of sugar syrup with the following analysis:

|  | % wt/wt | % of Total Sugars |
| --- | --- | --- |
| Xylose | 42.0 | 70.0 |
| Glucose | 9.6 | 16.0 |
| Arabinose | 5.3 | 8.8 |
| Galactose | 2.2 | 3.7 |
| Mannose | 0.9 | 1.5 |
| TOTAL SUGARS | 60.0 | 100.0 |

Aliquots of this bulk sample were taken and diluted or concentrated further to give samples with identical individual sugar ratios but different total sugar concentrations of 50.4%, 60%, 63.4% and 69.6% as analysed by HPLC.

Samples of 25 mls of the sugar syrup with the different above concentrations were taken and treated under a range of conditions to determine the percentage recovery of xylose crystals. Each 25 ml sample of syrup was mixed with either 25, 37.5 or 50 mls of ethanol at temperatures of ambient, 30° C. or 50° C. using a high speed Silverson mixer. The Silverson mixer was placed in the syrup and turned on. The ethanol was then added to the syrup over a period of 2 to 5.5 minutes. On completion of the addition of the required amount of ethanol, the mixer was left on for 1 minute further and then removed from the ethanol/sugar mixture. The mixture was then left to stand overnight before filtering off any crystals produced. The crystals were then dried and weighed. The percentage of total sugar precipitated was then calculated as the weight of dry crystals formed divided by the total mass of sugar in solution before the addition of ethanol.

BRIEF DESCRIPTION OF THE DRAWINGS

The results are shown in FIGS. 1, 2 and 3. These figures show the effect of % Sugar Concentration on the % Recovery of Sugar in the form of crystals for different ethanol/sugar ratios and temperatures. The figures clearly indicate that a critical syrup concentration (about 60 %) must be exceeded before the addition of ethanol if any reasonable recoveries of crystals are to be achieved. This critical concentration can be seen to be independent of ethanol/sugar ratio and temperature of the ranges investigated. There is also a clear increase in % sugar recovered as the % syrup concentration.increases above the critical concentration. Results for examples 3 and 4 are shown in FIGS. 4-5.

EXAMPLE 3

Figure 1:
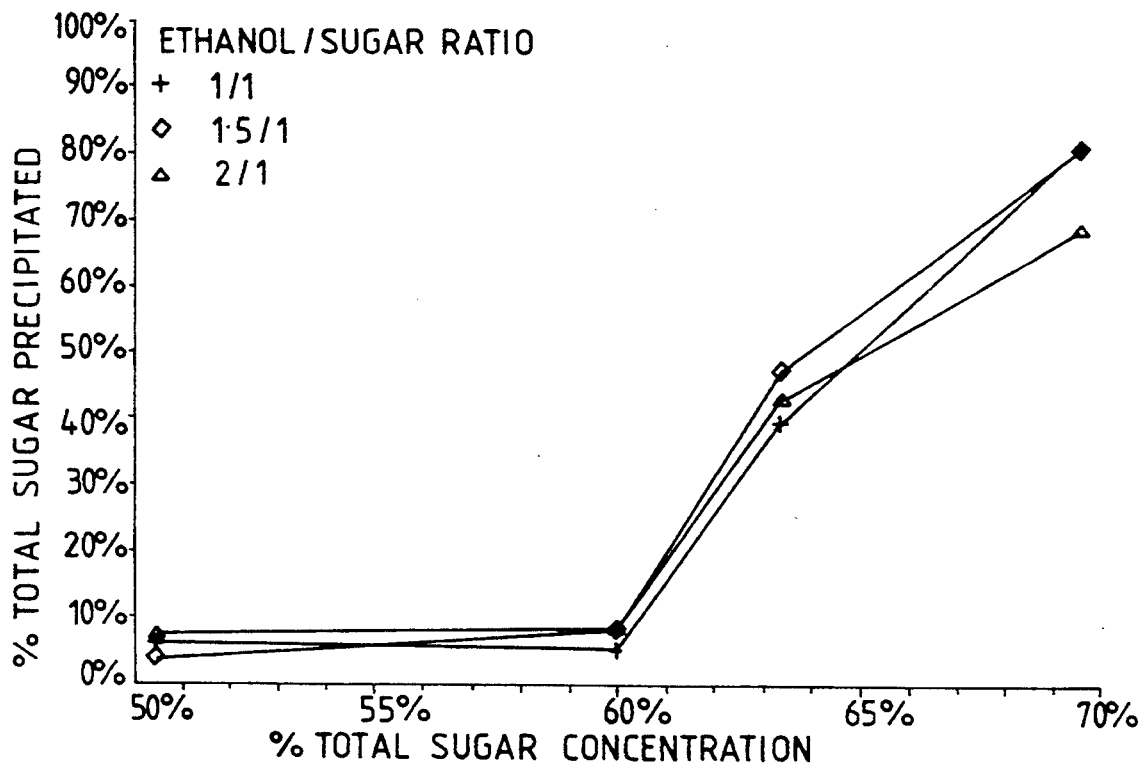
Figure 2:
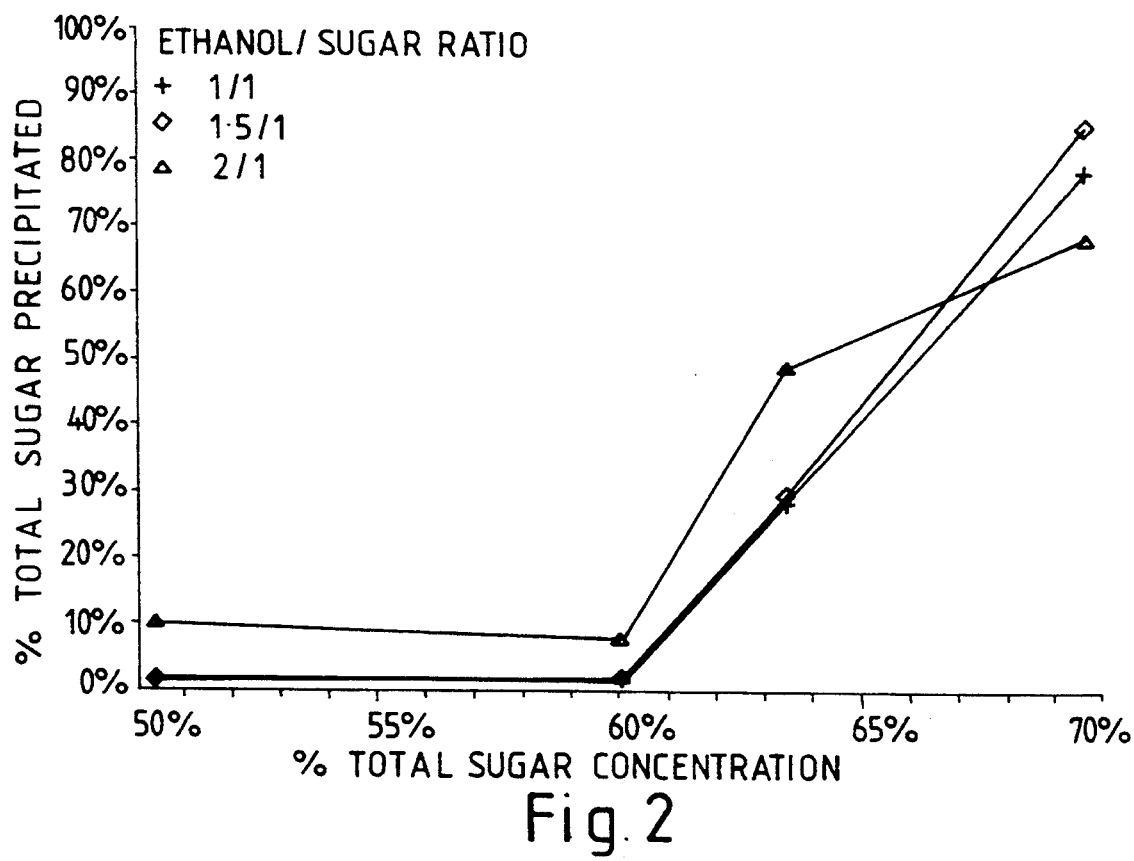
Figure 3:
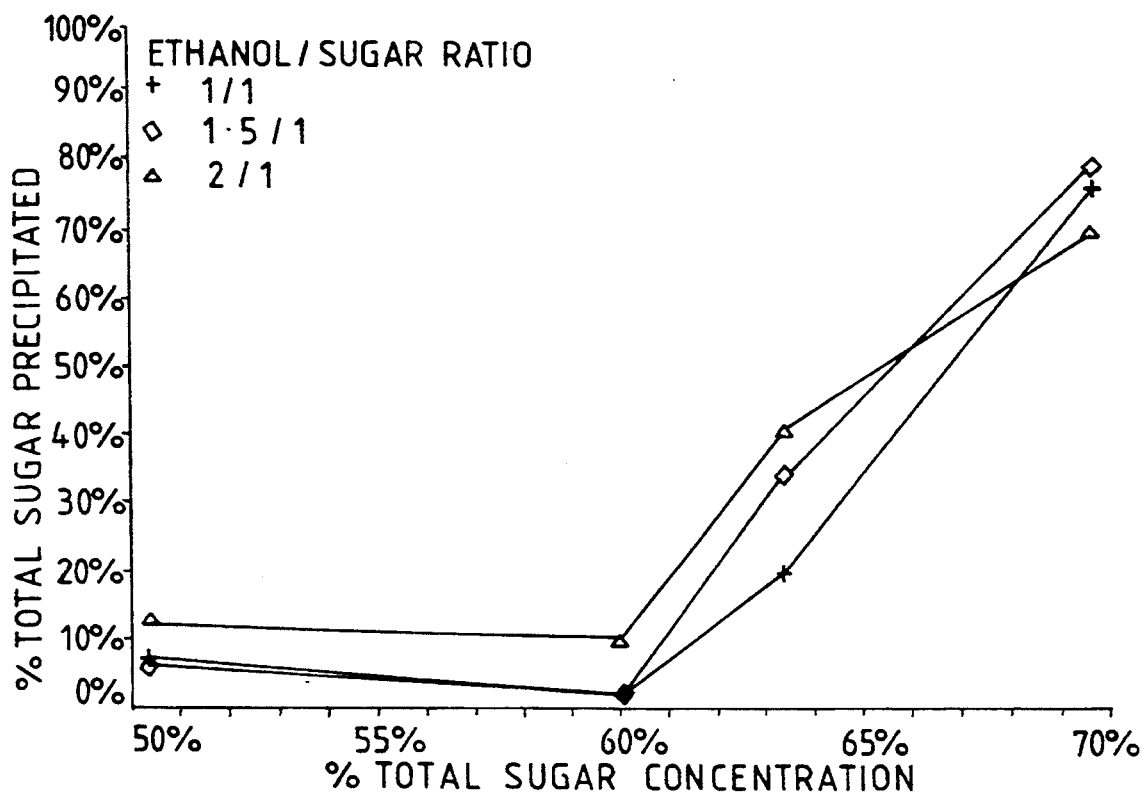
Figure 4:
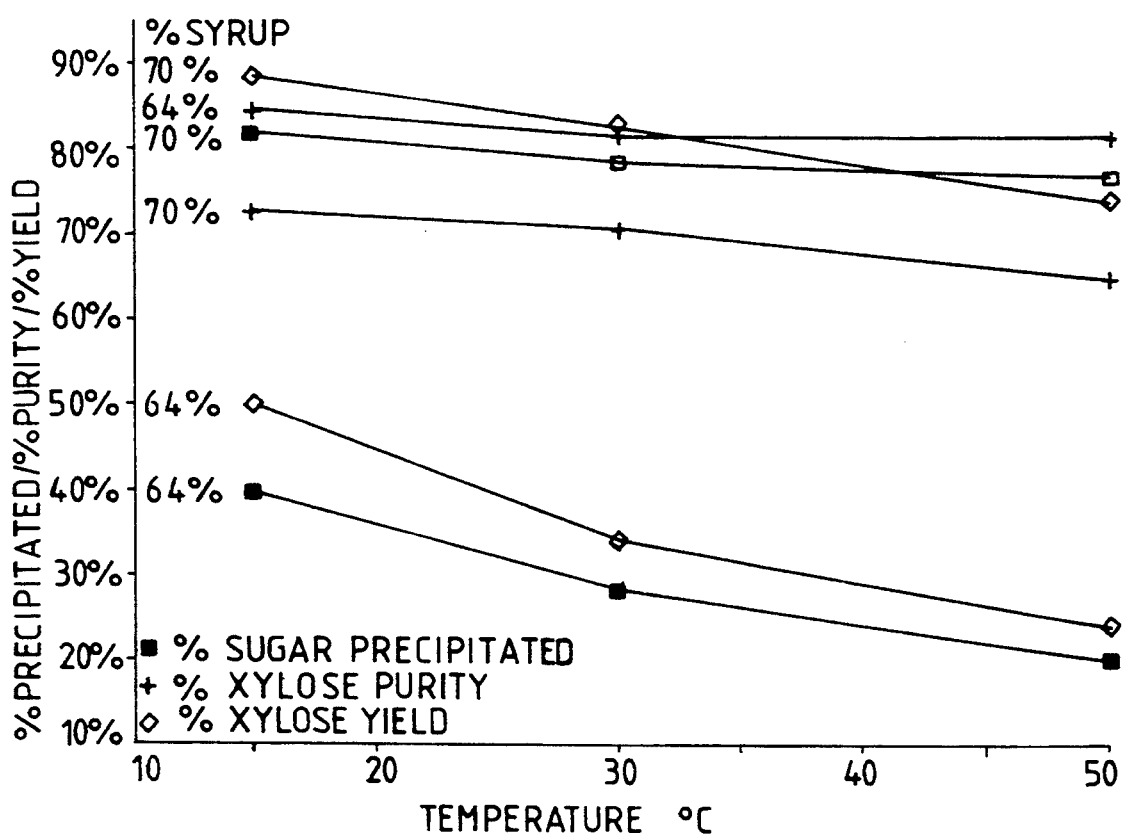

The dried sugar crystals obtained by the method described in Example 2 were analysed for xylose in order to calculate the % xylose purity of the crystals and thus the % yield of xylose in the crystal form. The results are shown in FIG. 4 giving the effect of temperature on the % total sugar precipitated, % xylose crystal purity and % xylose yield for 2 syrup concentrations. Several conclusions can be drawn from this example:
1. The % yield of xylose increases with increasing syrup concentration but decreases with increasing temperature.
2. The xylose crystal purity increases with decreasing syrup concentration but remains roughly constant with temperature.
3. The total percentage of sugar precipitated increases with increasing syrup concentration but decreases with increasing temperature.

This example demonstrates that any decision must be made on the required purity and yield of xylose on the basis of economics as it is difficult to maximise both yield and purity simultaneously.

EXAMPLE 4

Figure 5:
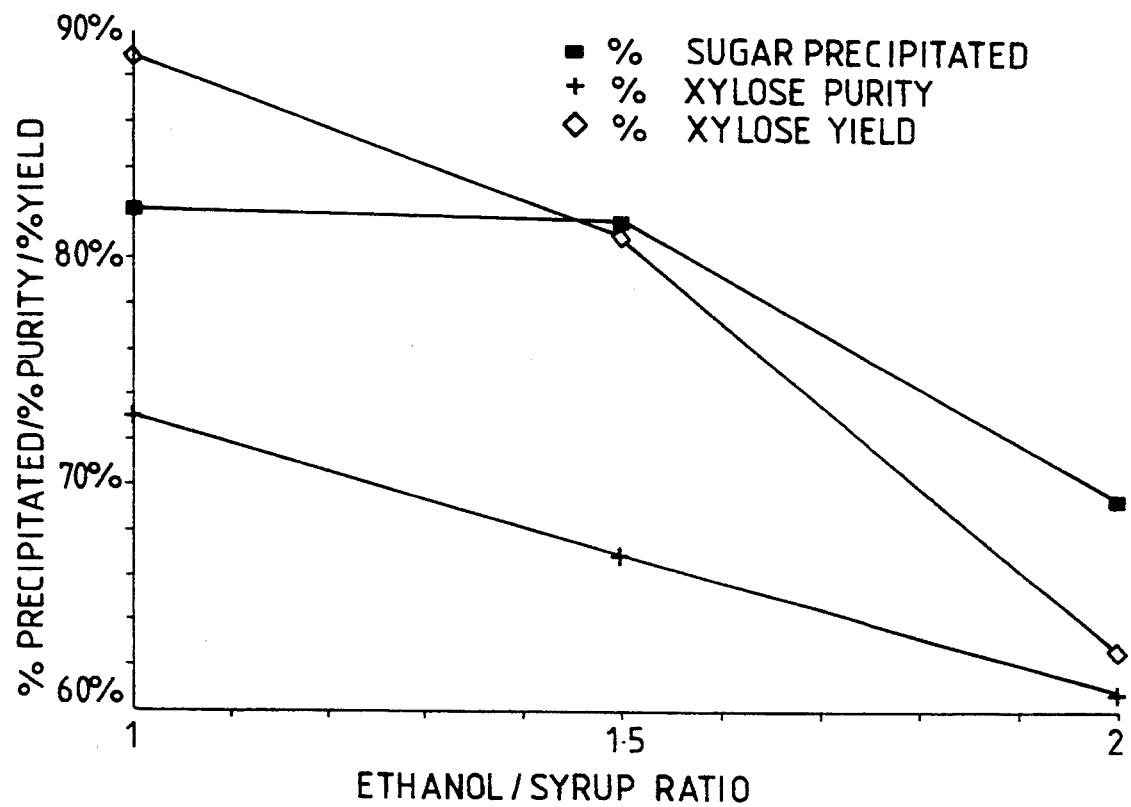

The method described in Example 2 was repeated to produce a syrup sample with a concentration of 70 %. 25 mls of syrup were mixed with differing quantities of ethanol at ambient temperature using a Silverson mixer and the method described in Example 2. The resulting crystals were dried and analysed for xylose to calculate the % sugar precipitated, % xylose purity and % xylose yield as described in Example 3. The results are shown in FIG. 5 to give the effect of increasing the ethanol/syrup ratio on purity and yield. This example shows that although it is possible to obtain crystals with an ethanol/sugar ratio of 2:1, the effect of increasing the ethanol ratio is to reduce both purity and yield of the final crystals.

We claim:

1. In a process for the production of xylose from a ligno-cellulosic material comprising an xylan-containing hemicellulose by the steps of:
   (1) hydrolysing the ligno-cellulosic material with an aqueous acid to produce an aqueous xylose-containing medium and an insoluble residue comprising lignin;
   (2) separating the insoluble residue from the xylose-containing medium;
   (3) treating the xylose-containing medium to remove organic and/or ionic contaminants therefrom;
   (4) concentrating the xylose-containing medium to a syrup; and
   (5) mixing the syrup with an alcohol to form an alcoholic solution and crystallizing xylose from the alcoholic solution;
   the improvement, whereby ethanol is used as said alcohol in step 5,
   which comprises:
   (a) controlling hydrolysis step (1) to limit hydrolysis of cellulose, whereby said insoluble residue contains also cellulose;
   (b) in step (4) concentrating to a water content in the range 20 to 40% by weight; and
   (c) in step (5) crystallizing at ambient temperature.

2. A process according to claim 1 wherein the crystals produced in step (5) are washed with aqueous ethanol.

3. A process according to claim 1, wherein step (2) or step (3) is followed by a post hydrolysis step.

4. A process according to claim 1 wherein the aqueous acid used in step (1) is a solution containing 0.5% to 5% acid in water.

5. A process according to claim 1 wherein the reaction mixture is maintained at a temperature within the range 100° to 150° C. during hydrolysis step (1).

6. A process according to claim 1 wherein the hydrolysis of step (1) is carried out for a period within the range 2 minutes to 2 hours.

7. A process according to claim 1 wherein in step (3) inorganic contaminents are removed by a treatment selected from the class consisting of electro dialysis and ion-exchange using a suitable resin.

8. A process according to claim 1 wherein in step (4) the xylose-containing medium is concentrated to a syrup having a water content in the range 30% to 37% by weight.

9. A process according to claim 1 wherein during step (5) ethanol is added to the syrup in a proportion in the range 0.5 to 2 volumes of ethanol per volume of syrup.

10. A process according to claim 9 wherein 1 volume of ethanol is added to 1 volume of syrup.

11. A process for the production of xylose from a ligno-cellulosic material comprising an xylan-containing hemicellulose, which comprises the steps of:
   (1) hydrolysing the ligno-cellulosic material with an aqueous acid to produce an aqueous xylose-containing medium and an insoluble residue comprising lignin and cellulose;
   (b 2) separating the insoluble residue from the xylose-containing medium;
   (3) treating the xylose-containing medium to remove organic and/or ionic contaminants therefrom; (4) concentrating the xylose-containing medium to a syrup having
   a water content in the range 20% to 40% by weight; and (5) mixing the syrup with ethanol to form an ethanolic solution
   and crystallizing xylose from the ethanolic solution; with a post hydrolysis step carried out between step (2) and step (3) or between step (3) and step (4) wherein the xylose-containing medium is heated to a temperature in the range 50 to 150° C. for a period within the range 2 minutes to 2 hours in the presence of an acid at a concentration in the range 0.5 to 5%.

12. A process for the production of xylose from a ligno-cellulosic material comprising a xylan-containing hemicellulose, which comprises the steps of:
   (1) hydrolysing the ligno-cellulosic material with an aqueous acid to produce an aqueous xylose-containing medium and an insoluble residue comprising lignin and cellulose;
   (2) separating the insoluble residue from the xylose-containing medium;
   (3) treating the xylose-containing medium to remove organic and/or ionic contaminants therefrom;
   (4) concentrating the xylose-containing medium to a syrup having a water content in the range 20% to 40% by weight; and
   (5) mixing the syrup with ethanol in a proportion in the range 0.5 to 2 volumes of ethanol per volume of syrup to form an ethanolic solution and crystallizing xylose from the ethanolic solution at ambient temperature.

* * * * *